(12) United States Patent
Nasser-Ghodsi et al.

(10) Patent No.: US 6,664,541 B2
(45) Date of Patent: Dec. 16, 2003

(54) METHODS AND APPARATUS FOR DEFECT LOCALIZATION

(75) Inventors: Mehran Nasser-Ghodsi, Hamilton, MA (US); Jeffrey Reichert, San Jose, CA (US)

(73) Assignee: KLA Tencor Technologies Corporation, Milpitas, CA (US)

( * ) Notice: Subject to any disclaimer, the term of this patent is extended or adjusted under 35 U.S.C. 154(b) by 30 days.

(21) Appl. No.: 09/990,170

(22) Filed: Nov. 21, 2001

(65) Prior Publication Data
US 2003/0062477 A1 Apr. 3, 2003

Related U.S. Application Data
(60) Provisional application No. 60/326,580, filed on Oct. 1, 2001.

(51) Int. Cl.[7] .......................... H01J 37/28; H01J 37/00
(52) U.S. Cl. .................. 250/310; 250/306; 250/307; 250/492.2; 250/491.1
(58) Field of Search ............................. 250/310, 306, 250/307, 492.2, 491.1

(56) References Cited

U.S. PATENT DOCUMENTS

| | | |
|---|---|---|
| 4,162,528 A | 7/1979 | Maldonado et al. |
| 4,472,825 A | 9/1984 | Jenkins |
| 4,476,386 A | 10/1984 | Reid et al. |
| 4,534,049 A | 8/1985 | Koga |
| 4,675,889 A | 6/1987 | Wood et al. |
| 4,777,364 A * | 10/1988 | Sartore ........................ 250/307 |
| 4,885,465 A | 12/1989 | Nagatsuka et al. |
| 4,959,848 A | 9/1990 | Parobek |
| 4,962,516 A | 10/1990 | Soezima |
| 5,055,679 A * | 10/1991 | Ninomiya et al. .......... 250/306 |
| 5,060,247 A | 10/1991 | Watanabe |
| 5,065,020 A | 11/1991 | Kanda |
| 5,210,414 A | 5/1993 | Wallace |
| 5,299,252 A | 3/1994 | Takahashi |
| 5,350,921 A | 9/1994 | Aoyama et al. |
| 5,485,499 A | 1/1996 | Pew et al. |
| 5,530,732 A | 6/1996 | Takemi |
| 5,594,246 A | 1/1997 | Sudo et al. |
| 5,596,195 A | 1/1997 | Obori et al. |
| 5,656,812 A | 8/1997 | Takahashi |
| 5,657,363 A | 8/1997 | Hossain et al. |
| 5,703,361 A | 12/1997 | Sartore |
| 5,754,620 A | 5/1998 | Hossain et al. |

(List continued on next page.)

FOREIGN PATENT DOCUMENTS

JP 6-267485 9/1994

OTHER PUBLICATIONS

J.L. Pouchou and F. Pichoir, "Electron Probe X–Ray Microanalysis Applied To Thin Surface Films and Stratified Specimens", Scanning Microscopy, Supplement 7., (1993), pp. 167–189.

"High–Resolution X–ray Microanalysis for Low Voltage Applications", Noran Instruments, (1997), 5 pages.

(List continued on next page.)

*Primary Examiner*—Nikita Wells
(74) *Attorney, Agent, or Firm*—Beyer Weaver & Thomas LLP

(57) ABSTRACT

The present invention includes a system for localization of defects in test samples. A sample is scanned using a particle beam. Some particles interact with conductive elements and may cause the emission of x-rays. Other particles can pass through the sample entirely and generate a current that can be measured. A higher current generated indicates less conductive material at the scan target that may mean a void, dishing, or erosion is present. Localization of a defect can be confirmed using an x-ray emission detector.

39 Claims, 10 Drawing Sheets

U.S. PATENT DOCUMENTS

| | | | |
|---|---|---|---|
| 5,777,336 | A | 7/1998 | Silver et al. |
| 5,866,903 | A | 2/1999 | Morita et al. |
| 5,877,498 | A | 3/1999 | Sugimoto et al. |
| 5,892,809 | A | 4/1999 | Wittry |
| 5,926,522 | A | 7/1999 | McCarthy et al. |
| 6,108,398 | A | 8/2000 | Mazor et al. |
| 6,351,516 | B1 | 2/2002 | Mazor et al. |
| 6,421,122 | B2 * | 7/2002 | Nara et al. .................. 356/394 |

OTHER PUBLICATIONS

M. Stavrev[a], D. Fischer[a], C. Wenzel[a], and T. Heiser[b], "Study of Ta(N,O) diffusion barrier stability: analytical and electrical characterization of low level Cu contamination in Si", Microelectronic Engineering, 37/38 (1997) pp. 245–251.

JeanLouis Pouchou, "X–Ray microanalysis of stratified specimens", Elsevier Science Publishers B.V., Analytica Chimica Acta. 283 (1993) pp. 81–97.

Schiebl et al., "A characteristic fluorescence correction factor for use in electron probe microanalysis", Microsc. Microanal, Microstruct. 2, 1991, pp. 413–423.

S. Sevov et al., "A comparison of recently developed correction procedures for electron probe microanalysis", Scanning, 1989, vol. 11, pp. 123–134.

August et al., "A method for determining the mass thickness of thin films using electron probe microanalysis", Scanning, 1987, vol. 9, pp. 145–155.

August et al., "Energy distribution of electrons transmitted through thin foils", Institut fur Angewandte aund Technische Physik, Technische Universitat Wien Wiedner Hauptstr.8–10, A–1040 Wien (Vienna), Austria.

Pfeiffer et al., "Models and their implementation", CEC–Vienna Reports, No. 92–08, Dec., 1992.

"MuFilm Data Collection & K–Ratio Measurement Documentation", pp. 2–10.

August et al., "Calculation and Comparison of the Surface Ionization", Institut fur Angewandte und Technische Physik, Technische Universitat Wien, Wiedner Hauptstr. 8–10, A–1040 Wien (Vienna), Austria.

August et al., "Calculation and Comparison of the Backscattering Factor R for Characteristic X–Ray Emission", Scanning, 1988, vol. 10, pp. 107–113.

August et al., "The Backscattering Factor as a Part of the Correction Procedures Employed in Quantitative Electron Probe Microanalysis", Radex–Rundschau, 1988, pp. 624–637.

August et al., "Calculation of the electron backscattering coefficient for thin films using a simple electron scattering model", J. Microsc. Spectrosc. Electron., 1989, vol. 14, pp. 189–201.

August et al., "Theoretical prediction of the electron backscattering coefficient for multilayer structures", Journal of Microscopy, Feb. 1990, vol. 157, pp. 247–254.

* cited by examiner

METHODS AND APPARATUS FOR DEFECT LOCALIZATION

CROSS-REFERENCE TO RELATED APPLICATIONS

This application claims the benefit of provisional application 60/326,580 filed on Oct. 1, 2001.

The present application is related to concurrently filed U.S. patent application Ser. No. 09/990,171 by Mehran Nasser-Ghodsi and Anne Testoni, and titled Methods and Apparatus for Void Characterization. The present application is also related to U.S. patent application Ser. No. 09/695,726 by Shing Lee, and titled Film Thickness Measurement Using E-Beam Induced X-Ray Microanalysis as of filing on Oct. 23, 2000. Each of the above noted applications are incorporated herein by reference for all purposes.

BACKGROUND OF THE INVENTION

1. Field of the Invention

The present invention generally relates to the field of inspection and analysis of specimens and, more particularly, to defect localization in semiconductor integrated circuits.

2. Description of Related Art

The metallization and thin film layers of conventional integrated circuits contain interconnects such as vias, contacts, and windows. The interconnects are arranged to allow electrical contact between transistors and other circuitry in an integrate circuit. However, a variety of factors may cause defects in the interconnects. Defective interconnects can ultimately lead to failure of the integrated circuit by causing open circuits.

One type of defect is a void formed in the via. Voids may be caused by a variety factors such as stress, electromigration, and impurities. As line widths continue to decrease in size, even small voids can prevent an integrated circuit from operating properly. Other types of defects are dishing and erosion that can result from processes such as chemical mechanical polishing (CMP) during the damascene and dual damascene processes. Dishing and erosion often results from polishing of the conductive layer to an extent such that insufficient conductive material is available to connect circuit elements.

Inspection of integrated circuit at various stages of manufacture can significantly improve production yield and product reliability. If a defect can be detected early in production, the cause of the defect can be determined and corrected before a significant number of defective IC's are manufactured.

Conventional defect detection systems frequently use the "voltage contrast" technique. The voltage contrast technique operates on the basis that potential differences in the various locations of a sample under examination cause differences in secondary electron emission intensities when the sample is the target of an electron beam. Thus, the potential state of the scanned area is acquired as a voltage contrast image such that a low potential portion of, for example, a wiring pattern might be displayed as bright (intensity of the secondary electron emission is high) and a high potential portion might be displayed as dark (lower intensity secondary electron emission). Alternatively, the system may be configured such that a low potential portion might be displayed as dark and a high potential portion might be displayed as bright.

A secondary electron detector is used to measure the intensity of the secondary electron emission that originates only at the path swept by the scanning electron beam. A defective portion can be identified from the potential state of the portion under inspection. In one form of inspection, the mismatched portion between the defective voltage contrast image and the defect free one reveals the general defect location.

Other techniques involve slicing a wafer into cross sections and using an electron microscope to detect defects. Intrusive methods, however, are both time consuming and wasteful. Acoustic and optical methods are also available, but can only be used in particular circumstances. For example, optical methods are often only effective in very specific circumstances.

Conventional systems do not allow efficient localization of defects. Accordingly, additional improved detection systems allowing more effective localization of defects are desirable

SUMMARY

The present invention includes a system for localization of defects in test samples. A sample is scanned using a particle beam. Some particles interact with conductive elements and may cause the emission of x-rays. Other particles can pass through the sample entirely and generate a current that can be measured. A higher current generated indicates less conductive material at the scan target that may mean a void, dishing, or erosion is present. Localization of a defect can be confirmed using an x-ray emission detector.

An apparatus for localizing a defect in a first scan target associated with a sample having a first surface and a second surface is provided. A particle beam generator is configured to scan a first scan target. The particles interact with a first material in the scan target. A generated current detection system is configured to obtain a measurement of generated current resulting from the scan of the first scan target. The measurement of generated current is compared with a control measurement to provide information for localization of a defect in the first scan target.

A system for localizing a defect in a sample sample having a first surface and a second surface is provided. The system includes a memory and a processor coupled with memory. The processor is configured to identify a first measurement of generated current resulting from a particle beam scan of a first scan target and a second measurement of x-ray emissions from the first surface. The processor is further configured to identify a control measurement and provide the first measurement and the control measurement for comparison to thereby provide information for localizing a defect associated with the first scan target in the sample.

According to still another embodiment, a method for localizing a defect in a sample is provided. A first measurement of generated current resulting from a particle beam scan of a first scan target is provided. A control measurement is provided. The first measurement and the control measurement are provided for comparison to thereby obtain a characterization of a defect associated with the first scan target in the sample.

These and other features and advantages of the present invention will be presented in more detail in the following specification of the invention and the accompanying figures which illustrate by way of example various principles of the invention.

BRIEF DESCRIPTION OF THE DRAWINGS

The invention may best be understood by reference to the following description taken in conjunction with the accompanying drawings. It should be noted that the drawings are illustrative of specific embodiments of the present invention.

DESCRIPTION OF SPECIFIC EMBODIMENTS

Figure 1:
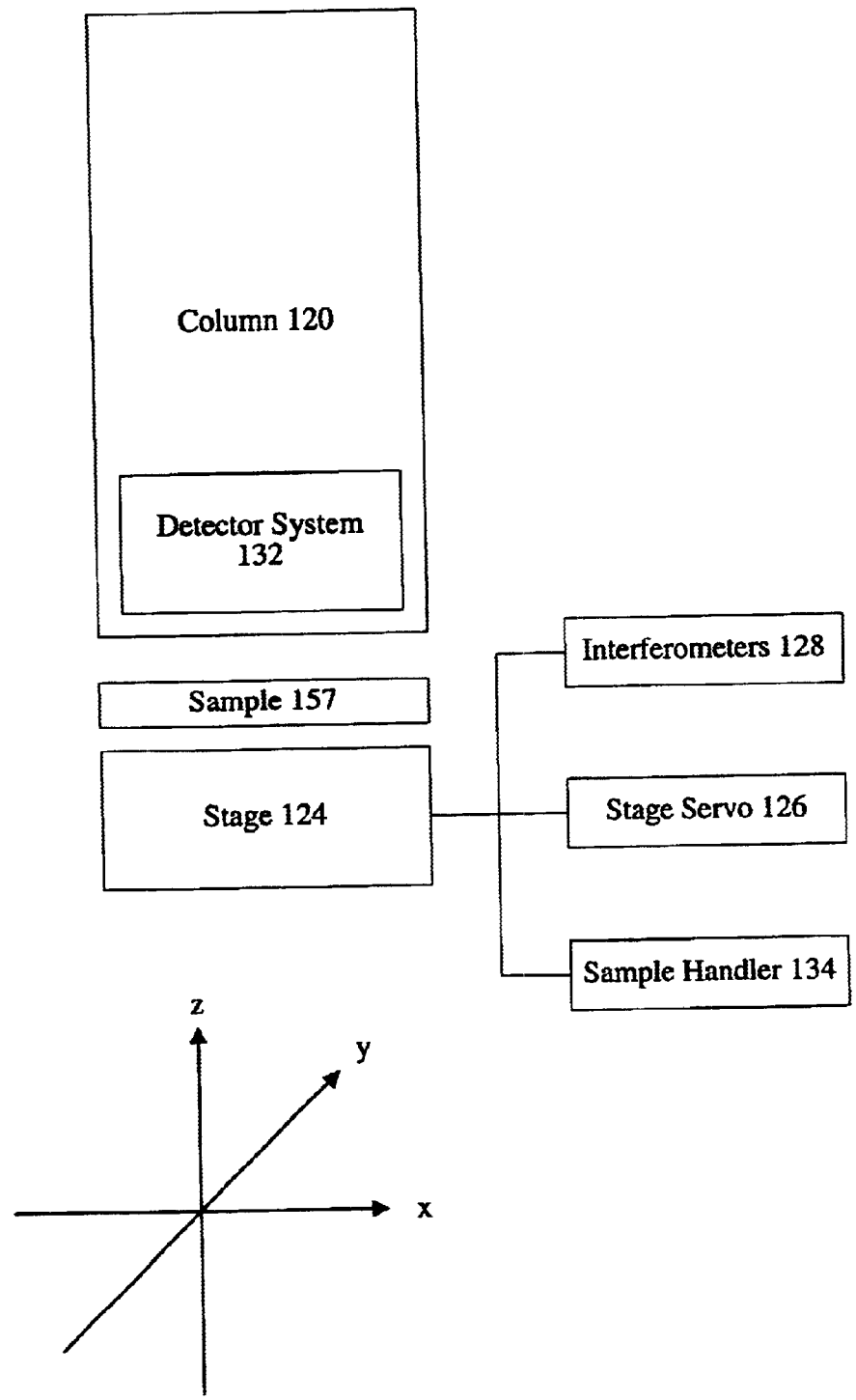
FIG. 1 is a diagrammatic representation of a system that can use the techniques of the present invention.

As will be further described below, the preferred embodiment of the present invention provides efficient wafer inspection capabilities in order to localize defects in test samples.

Several embodiments of the present invention are described herein in the context of void localization. Although the techniques of the present invention accurately localize voids in test samples, other types of defects such as dishing and erosion can be detected as well. The techniques of the present invention can be used to detect any type of defect causing the lack of a particular material. As will be appreciated by one of skill in the art, the techniques for defect localization are general and can be applied in a variety of contexts such as void, erosion, and dishing detection for metallization and thin film layers.

The techniques of the present invention allowing nondestructive localization of a defect in a test sample. In one embodiment, the test sample is a wafer comprising a plurality of integrated circuits. During the production of conventional integrated circuits, openings are left in a dielectric layer for a conductive material having low resistivity. The openings may be filled with the conductive material, such as aluminum or copper, to allow electrical contact between circuit elements. The openings can include vias, windows, or contacts.

When the openings are filled with the conductive material, the integrated circuit elements can operate properly. However, a variety of factors may cause the formation of defects in the conductive material. Voids, dishing, and erosion may arise during manufacturing processes.

A particle beam such as an electron beam can be used to scan a target on a test sample. The scan target can be a single via, window, or contact. A current detector such as an electrically isolated stage holding the sample can be used to measure the current generated as the result of the scan. According to various embodiments, a conductive material exposed to an electron beam interacts with the electrons. For example, copper bombarded by electrons interacts with the electrons and emits x-rays characteristic of copper. A scan target without as much conductive material would have less interaction with the electrons from the electron beam. Consequently, more of the electrons from the electron beam would pass through the conductive material and the test sample entirely. In other words, a scan target with a void, dishing, or erosion would have less conductive material to interact with electrons from an electron beam and would allow more electrons to pass through the sample. The intensity of the electrons or the current generated can be measured by a detector such as an electrically isolated stage connected to a device such as a voltmeter or ammeter to determine whether a defect exists at a scan target.

With information about the void, a system operator can improve the integrated circuit manufacturing process to reduce the number of defects and to increase yields.

FIG. 1 is a diagrammatic representation of a system that can use the techniques of the present invention. The detail in FIG. 1 is provided for illustrative purposes. One skilled in the art would understand that variations to the system shown in FIG. 1 fall within the scope of the present invention. For example, FIG. 1 shows the operation of a particle beam with a continuously moving stage. However, the test structures and many of the methods described herein are also useful in the context of other testing devices, including particle beams operated in step and repeat mode. As an alternative to moving the stage with respect to the beam, the beam may be moved by deflecting the field of view with an electromagnetic lens. Alternatively, the beam column to be moved with respect to the stage.

Sample 157 can be secured automatically beneath a particle beam 120. The particle beam 120 can be a particle beam such as an electron beam. The sample handler 134 can be configured to automatically orient the sample on stage 124. The stage 124 can be configured to move and rotate xy plane. In a preferred embodiment, the stage 124 is aligned relative to be particle beam 120 so that the x-directional motion of the stage is corresponds to the axis determined by the length of a via. For example, the sample 157 can be aligned so that the x-directional movement of the stage corresponds to the length of a via as viewed from the top of the sample. Similarly, the sample 157 can be aligned so that the x-directional movement of stage corresponds to the width of a via. Fine alignment of the sample can be achieved automatically or with the assistance of a system operator. The position and movement of stage 124 during the analysis of sample 157 can be controlled by stage servo 126 and interferometers 128.

While the stage 124 is moving in the x-direction, the inducer 120 can be repeatedly deflected back and forth in the y direction. According to various embodiments, the inducer 120 is moving back and forth at approximately 100 kHz.

According to a preferred embodiment, the stage 124 is electrically isolated to allow a determination of the amount of current generated as the result of the scan of the scan target. In one embodiment, the electrically isolated stage 124 can be connected to a voltmeter. As will be appreciated by one of skill in the art, other systems such as electron detectors, for measuring electrons passing through the sample are contemplated.

A detector 132 can also be aligned alongside the particle beam 120 to allow further defect detection capabilities. The inducer 120 and stage 124 as well as other elements such as detector 132 can be controlled using a variety of processors, storage elements, and input and output devices.

Figure 2:
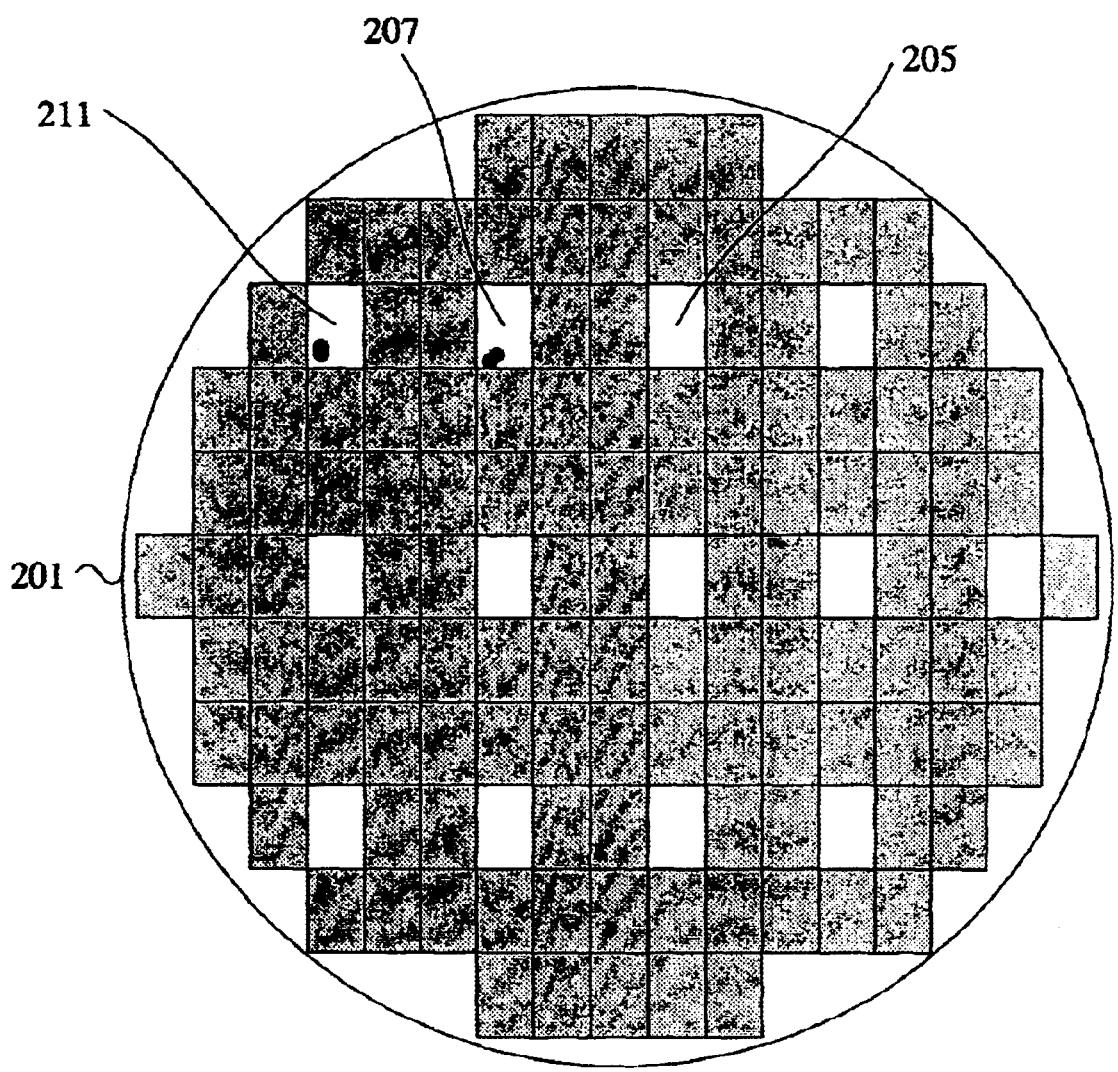
FIG. 2 is a diagrammatic representation of a wafer that may be the sample under test.

FIG. 2 is a diagrammatic representation of a wafer that may be a sample under test. A wafer 201 comprises a plurality of dies 205, 207, and 211. Die 205 contains no voids while dies 207 and 211 contain voids. Other dies may show other defects such as dishing or erosion. According to various embodiments, the techniques of the present invention for defect localization are performed after each metallization or thin film layer is deposited onto a wafer. The side of the wafer where the metallization process is performed is herein referred as the top surface of the wafer. The wafer can be scanned to detect and characterize defects after a thin film layer or metallization layer comprising a material such as copper is deposited onto the first surface of the wafer. The ability to detect defects during the manufacturing process allow immediate modification of the manufacturing process. By contrast, conventional techniques often were not able to recognize and correct defects and defective processes until after processing of the devices was completed.

The test methodologies of the present invention can be used as part of an advanced process control system, in which data from the testing process is provided to automated control systems for improving process yield. As an example, the techniques for void detection can provide data to automated control systems that dynamically improve the metallization processes.

Figure 3:
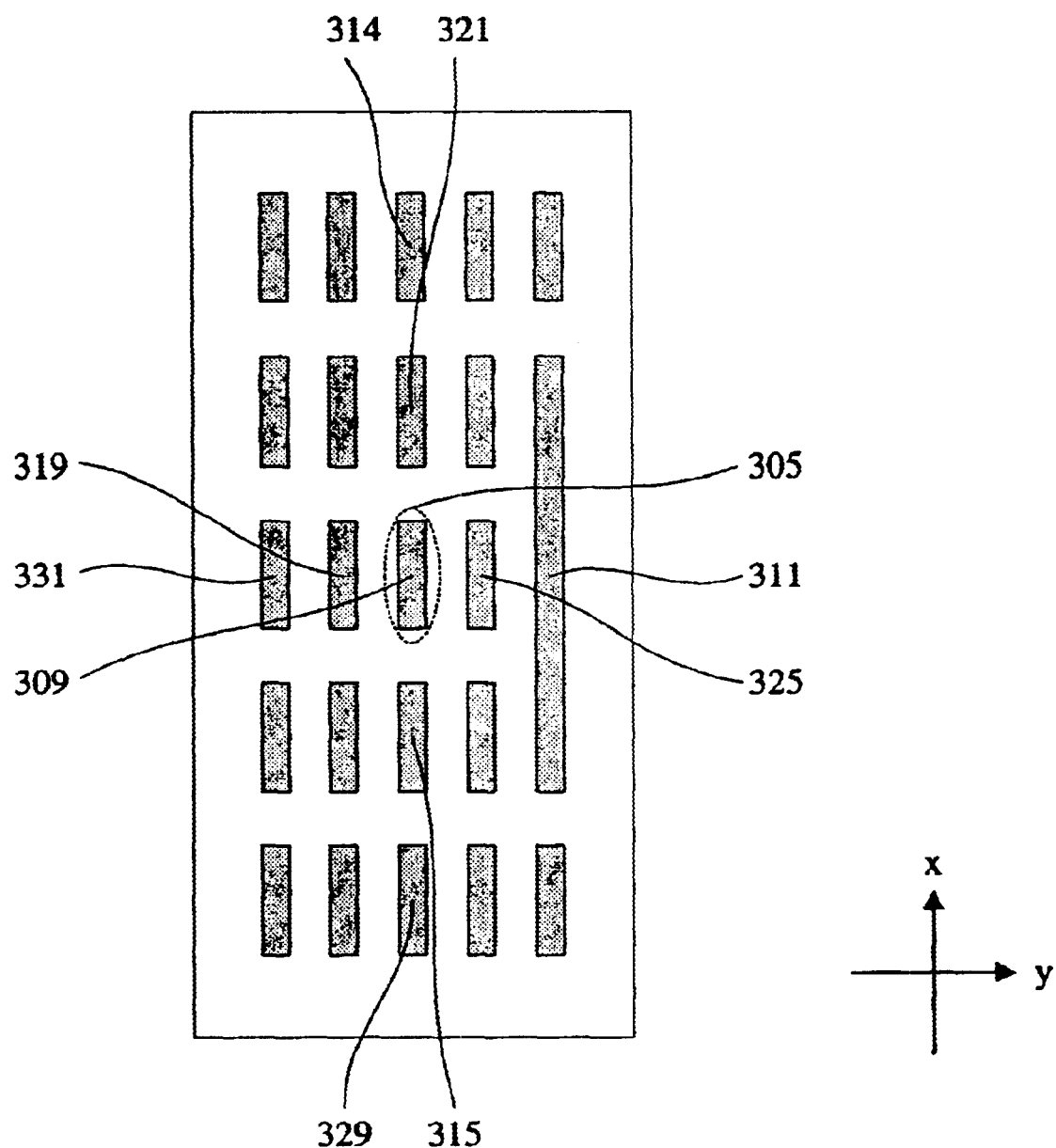
FIG. 3 is a diagrammatic representation of a plurality of vias on an integrated circuit.

FIG. 3 is a diagrammatic representation of a plurality of vias formed as part of a metallization layer on a die. As noted above, vias are one possible scan target for the particle beam. Other scan targets include conductive elements such as contacts and windows. As will be appreciated by one of skill in the art, vias can have a variety of different configurations. There may be 6 million vias formed in a single metallization layer of a die. According to various embodiments, each via is a scan target. In one example, the scan target is 1.29 um. A particle beam is targeted at each individual via and current detector is used to measure the current generated due to the scan. Via 309 may reside in scan target 305. Sample 301 may be rotated into a position so that the length axis of via 309 is substantially parallel to the x-directional movement of the stage. It should be noted that measuring x-ray emissions resulting from the scanning of a particular via may require realignment of the sample with respect to the particle beam.

Vias 319, 321, 311, and 315 are adjacent to via 309. Via 321 is referred to herein as the via in the +x position of via 309. Via 315 is referred to herein as the via in the −x position of via 309. Similarly, vias 319 and 311 are referred to herein as the vias in the +y and −y positions of via 309.

According to one embodiment, via 309 in scan target 305 is bombarded by electrons from an electron beam. The electrons from the electron beam interact with the conductive material of via 309. A current detector can measure the number of electrons passing through the sample entirely. The current can be measured to determine whether a defect exists in via 309. However, when the electrons are directed at scan target 305, some of the electrons reach adjacent vias 321, 311, 315, and 319. The electrons reaching the adjacent vias interact with the material in the adjacent vias. Since many electrons interact with conductive material in the adjacent vias, not as many electrons pass through the test sample entirely. Fewer electrons are measured by the current detector, skewing the current measurement for via 309. According to one embodiment, the current measurement resulting from the scan of scan target 305 is compared to a control measurement to allow consideration of skew. The control measurement may be obtained from the database having values for vias of a particular material. Alternatively, the control measurement may be determined by scanning the adjacent vias. Adjacent vias provide an effective technique for providing a control measurement because adjacent vias often have characteristics similar to that of the via under test.

In one embodiment, if the current measurement for the via under test is greater than or equal to the control measurement, there is no void in the via. If the current measurement for the via is less than the control measurement, there is a void in the via. It should be noted that although a void is used as one convenient example of a defect, any type of defect associated with a lack of particular material can be localized using the techniques of the present invention.

For example, a via 309 without a void in a copper metallization layer will have a comparable current measurement as an adjacent via 311 without a void. However, a via 309 with a void will not have the same current measurement as an adjacent via 311 without a void.

According to one embodiment, the current measurements resulting from scanning vias 341, 321, 311, 325, 315, 329, 331, and 319 are used to obtain a control measurement. If the average of the current measurements resulting from scanning the above adjacent vias is greater than the current measurement resulting from scanning via 309, via 309 can be characterized as having a void. It should be noted that the control measurement can be determined at any time. For example via 309 may be scanned well before a control measurement can be determined, since adjacent vias have not yet been scanned. All the vias may be scanned in raster mode and the resulting current measurements can stored in the database. After the scan is completed, defect determinations can be made based on the current measurements of a particular via and the control measurements determined from current measurements of adjacent vias. According to other embodiments, after via 309 scanned, the adjacent vias are immediately scanned to determine whether via 309 contains a void.

Voids can be characterized further by varying the scan target. After a void is detected, an electron beam can be focused on nearby areas immediately neighboring the detected void. Variations in current measurements can provide information for determining the location and dimensions of the void.

Figure 4:
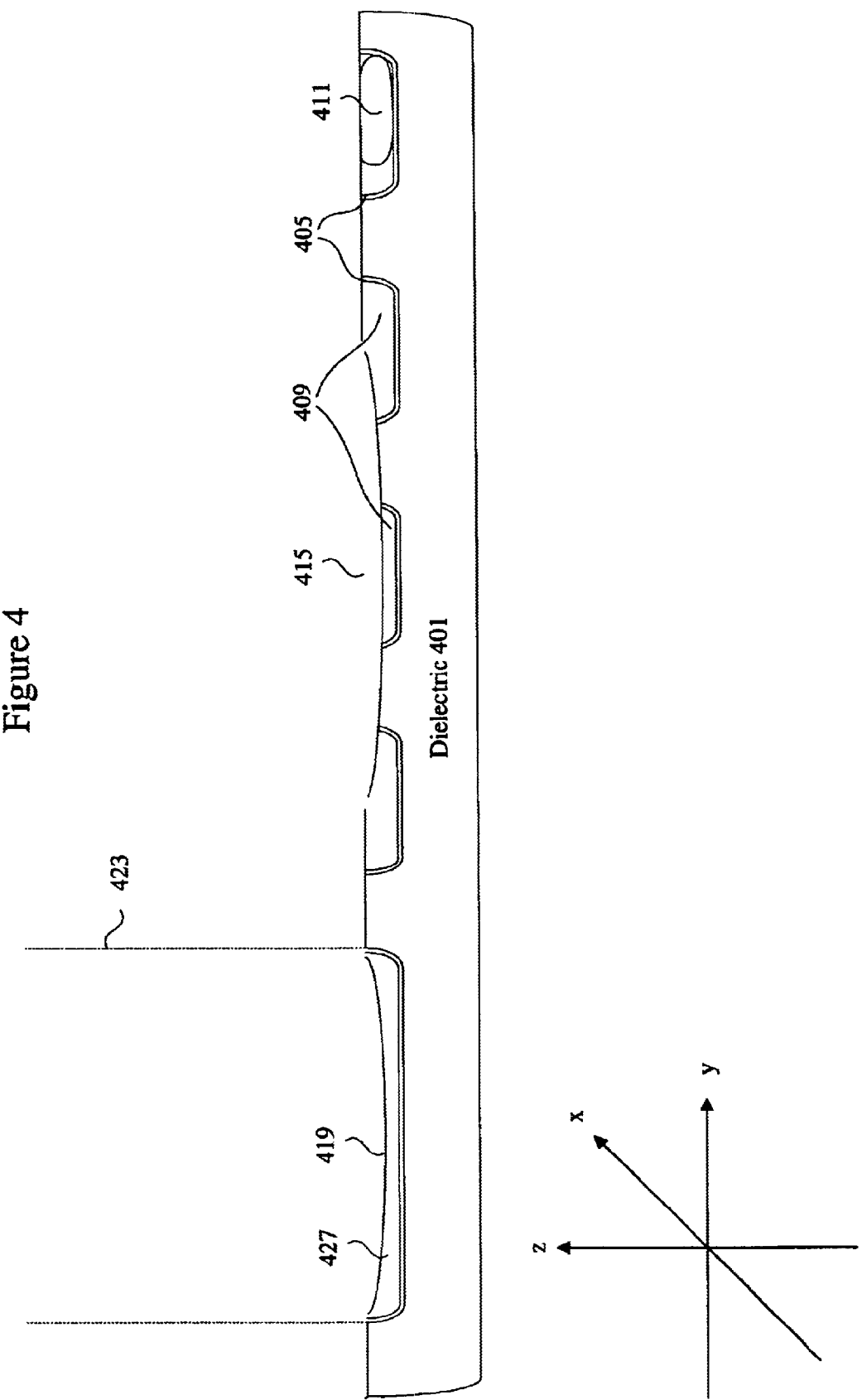
FIG. 4 is a cross-sectional representation of a plurality of vias.

FIG. 4 is a diagrammatic representation of a cross-section of a test sample. The metallization or thin film layer 409 is deposited on top of a barrier layer 405. According to various embodiments, the thin film layer 409 comprises a material such as copper (Cu) or aluminum (Al) and the barrier layer comprises a material such as tantalum (T) or tantalum nitride (TaN). Typically, the metallization or thin film layer 409 is much thicker than the barrier layer 405. A tantalum barrier layer 405 is typically used to prevent copper from thin film layer 409 from seeping into the dielectric 401. In one embodiment, the thin film layer is 1000 nm while the barrier layer is 15 nm. However, the techniques of the present invention can be used for detecting voids 411, dishing 419, and erosion 415 associated with metallization layers 409 and barrier layers 405 of varying thickness.

According to one embodiment, via 427 shows characteristics of dishing. An electron beam 423 is used to scan via 427. The generated current will vary based on the intensity of electrons passing through the sample entirely. The sample can also be rotated along the z-axis to allow scanning of the via 427. In one example, the sample is rotated about the z-axis situated at the center of the via 427. According to another example, the sample is rotated about the z-axis determined by the center of the sample.

According to various embodiments, defects are localized after a metallization layer 409 is deposited onto a barrier layer 405. The energy of the scan by a particle beam such as an electron beam is varied based on the nominal thickness of the thin film layer. The electron beam energy is varied to allow maximum interaction with the conductive material 409. If the electron beam energy is insufficient, few electrons will penetrate the surface of the sample and interact with the conductive material, such as copper. If the electron beam energy is too high, many electrons will penetrate the conductive material completely without interacting with the metallization layer 409.

Figure 5:
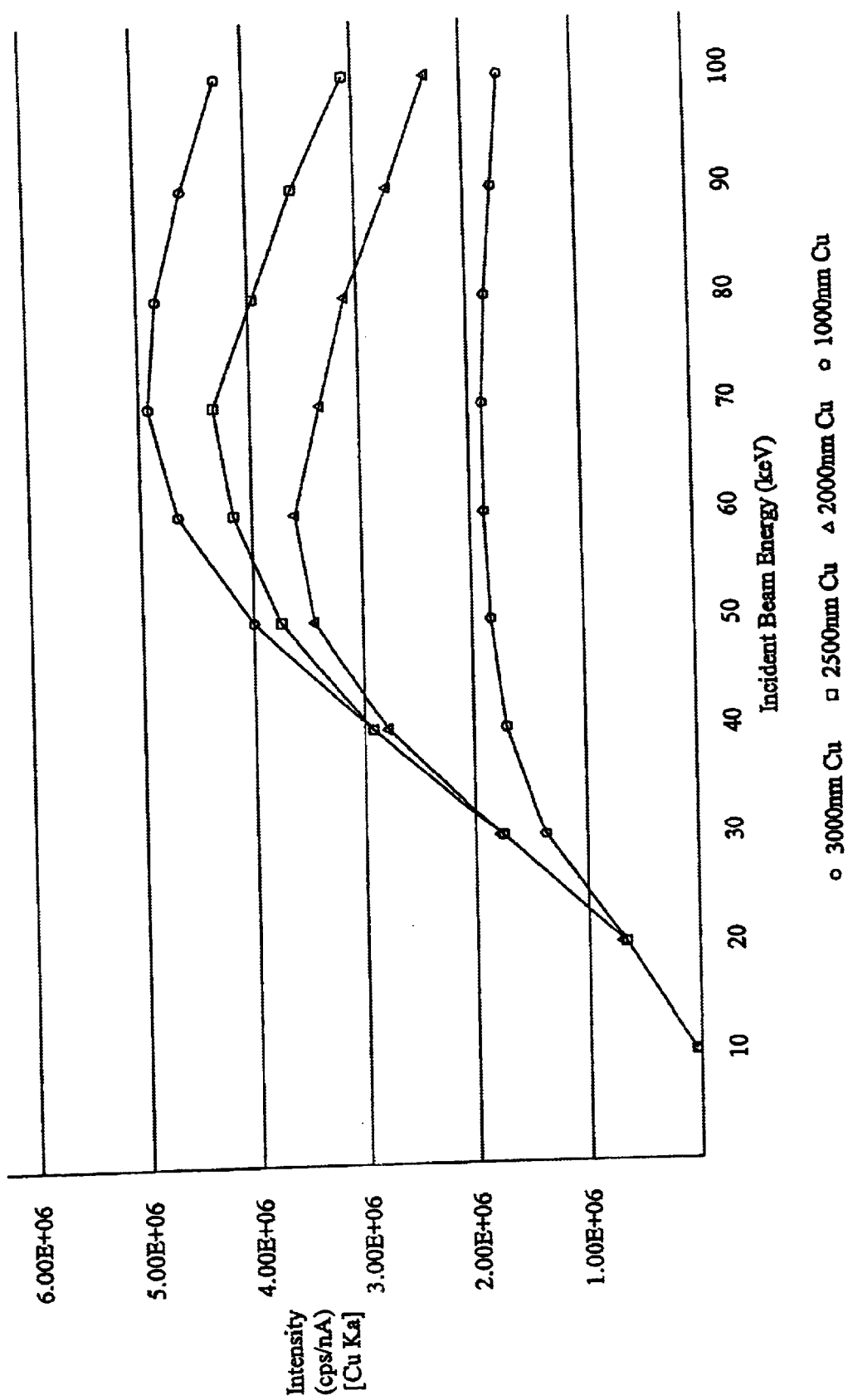
FIG. 5 is a graphical representation of incident beam energies and generated current.

FIG. 5 is a graphical representation showing preferred electron beam energies for copper layers of varying thickness. Electrons from the electron beam interact with copper to emit x-rays. According to various embodiments, generated current is higher when fewer x-rays are emitted. In other words, generated current is higher when fewer electrons interact with the copper. For 1000 nm copper, the generated current measurement is 2.00e+06 cps/nA when the incident beam energy is approximately 40 keV. For 2000 nm copper, the generated current measurement is 3.50e+06 cps/nA when the incident beam energy is approximately 60 keV. If the electron beam energy is too high, all the electrons pass through the sample, resulting in a high generated current value. If the electron beam energy is too low, few electrons pass through the sample, resulting in a low generated current value. An electron beam energy can be selected to provide a high generated current value when a void is in the metallization and a low generated current value when no found is in the metallization.

The techniques of the present invention allow localization of defects such as voids, erosion, and dishing. The techniques can be used in conjunction with other techniques to confirm the existence of a defect. For example, the techniques can be used in conjunction with a void characterization system as described in concurrently filed U.S. patent application Ser. No. 09/990,171 (Attorney Docket No. KLA1P041) by Mehran Nasser-Ghodsi and Anne Testoni, and titled Methods and Apparatus for Void Characterization, the entirety of which is incorporated by reference all purposes. Using the techniques with the void characterization system allow efficient in-line detection, confirmation, and characterization of voids without destructive techniques or redundancy.

Figure 6:
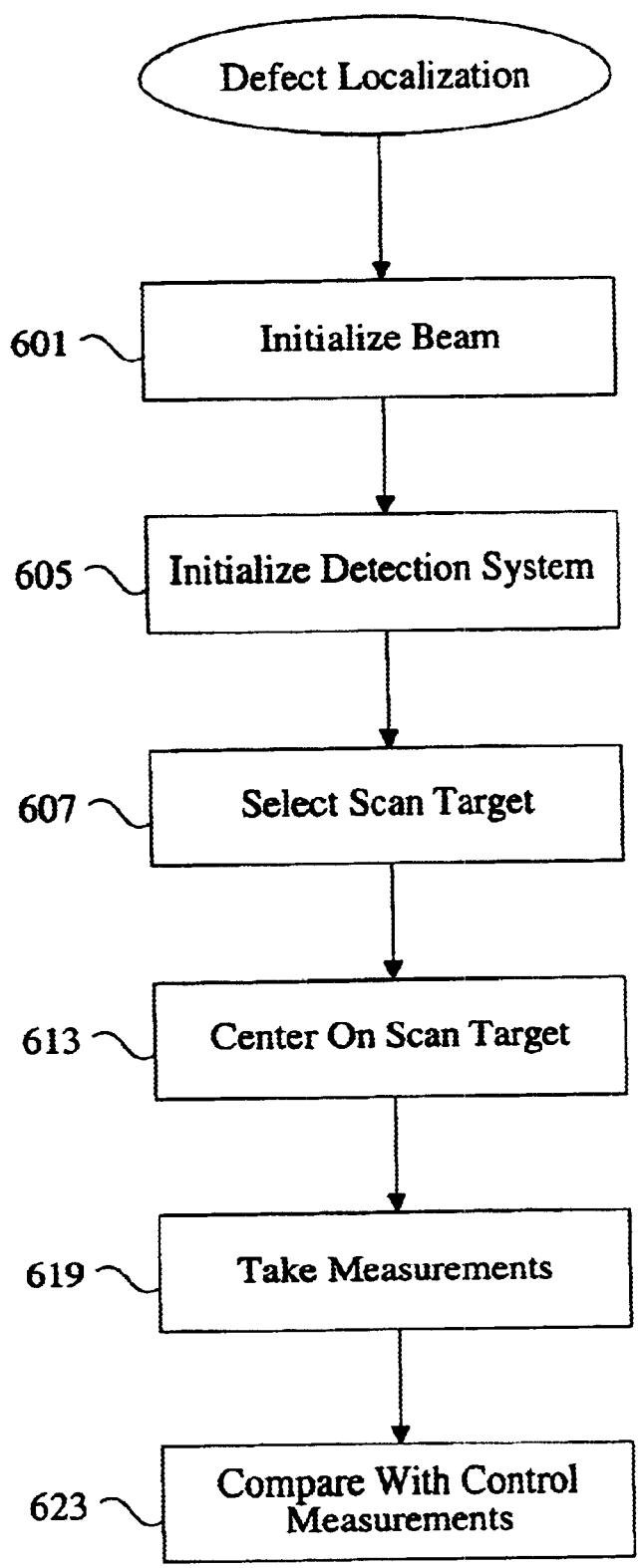
FIG. 6 is a process flow diagram showing the scanning of a sample.

FIG. 6 is a process flow diagram showing the detection and characterization of a void according to specific embodiments. At 601, and particle beam is initialized. Initializing the particle beam may involve setting the electron beam energy based on the thickness of a thin film layer under test. The beam energy can be set as noted above with reference to FIG. 5.

The generated current detectors can be initialized at 605. In one example, the bottom surface of the test sample is coupled to one lead of the current detector while the top surface of the test sample is coupled with the other lead of the current detector. The expected resistivity of the test sample can be provided. A standard sample can be scanned using the particle beam as part of the initialization process at 605. In one embodiment, a layer of copper having a predetermined thickness is scanned so that a generated current value is measured by the detectors at 605. The standard measurement can be used to tune the current detectors to set detector sensitivity. A variety of calibration and initialization techniques can be used. According to various embodiments, initialization of the inducer at 601 and the detectors at 605 is performed before each wafer is tested. According to other embodiments, initialization occurs again after a number of wafers are scanned.

At 607, the particle beam is directed at the scan target. The scan target may be an area of interest as determined by the voltage contrast technique. The scan target may also be any area that may contain a void. The inducer can be directed at the scan target by moving the stage or by moving the inducer. At 613, a suspect via is centered in the frame of view of the particle beam.

The via is scanned by a particle beam, such as electron beam, and the generated current is measured at 619. According to various embodiments, the current detectors is part of an electrically isolated stage.

The generate current measurement is compared with a control measurement in order to determine whether a void is present in the via. According to one embodiment, if the generated current measurement is 10% to 25% less than the control measurement, a void is determined to be present. In one example, if the generated current measurement is 20 nA while the control measurement is 25 nA, a void is determined to be present. The control measurement can be determined in a number of different ways. According to one embodiment, after the current generated is measured, the neighboring vias are scanned and the current generated is determined. For example, after the first via is scanned and the current generated is determined, the neighboring +x, -x, +y, and -y vias are scanned and the corresponding current generated is measured. Subsequently, the neighboring +2x, -2x, +2y, -2y vias are scanned as well. As noted above, the current generated for scans of neighboring vias can be used to determine a control measurement. Alternatively the control measurement may be a value stored in the database determined from another process or from scans of certain neighboring vias such as +x, +y, -x, -y, etc. In one embodiment, the current generated from a scan of a via and the current generated from scans of adjacent vias can be compared graphically.

Figure 7A:
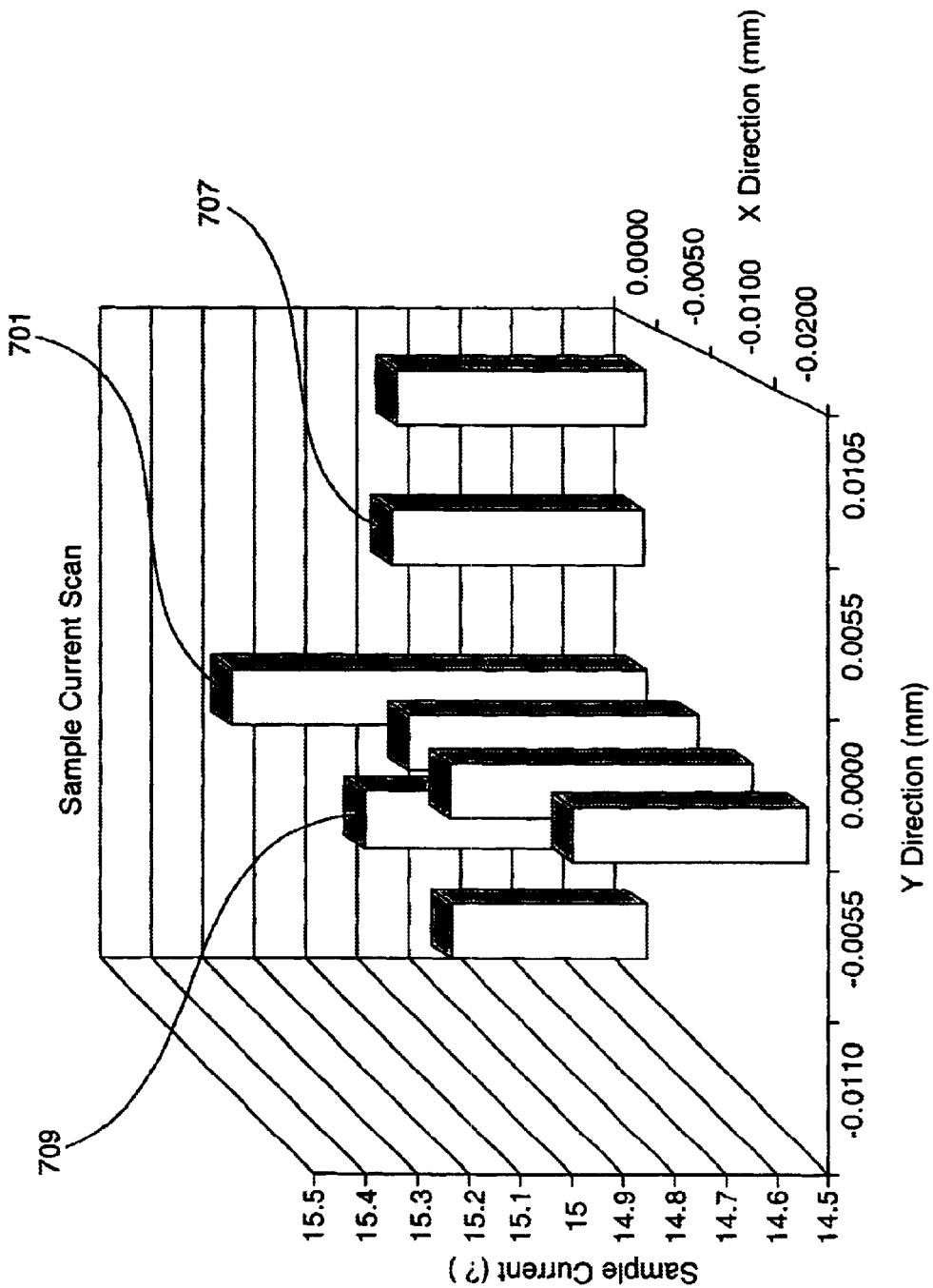
FIGS. 7A and 7B are graphical representations of generated current corresponding to a scan target and adjacent scan targets.
Figure 7B:
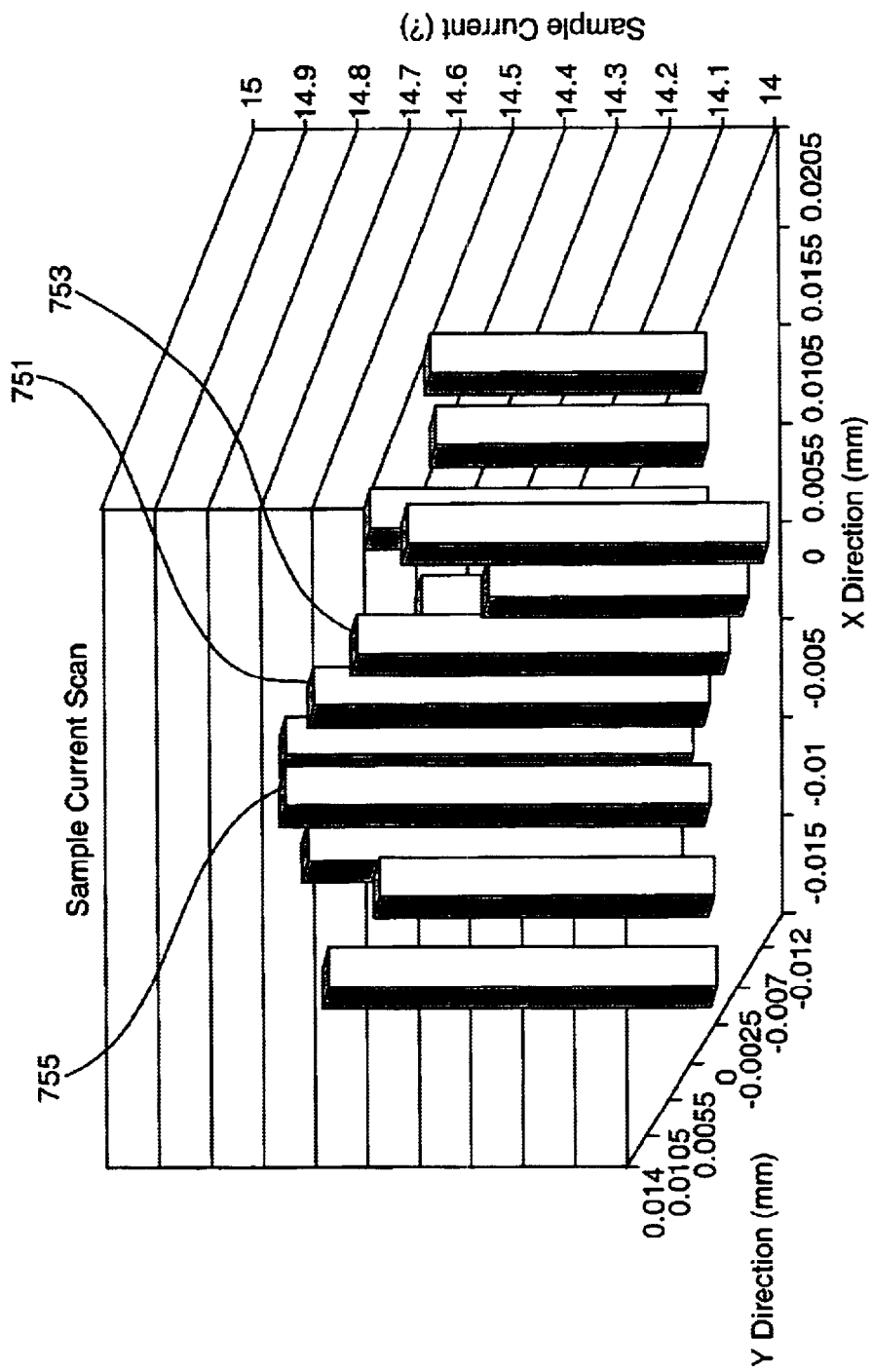

FIGS. 7A and 7B are graphical representations of the current generated resulting from scans of a via and the adjacent vias. FIG. 7A is a graphical representation of current generated for a scan of a via having a void. A scan of a via results in generated current measurement 701. The generated current measurement 701 is significantly less than the generated current measurements 707, 705, and 709, corresponding to +y, -x, and -y. By contrast, FIG. 7B is a graphical representation of the current generated resulting from scans of a via without a void. It should be noted that the generated current measurement 751 is similar to the generated current measurement measurements 753 and 755 of neighboring vias.

Figure 8:
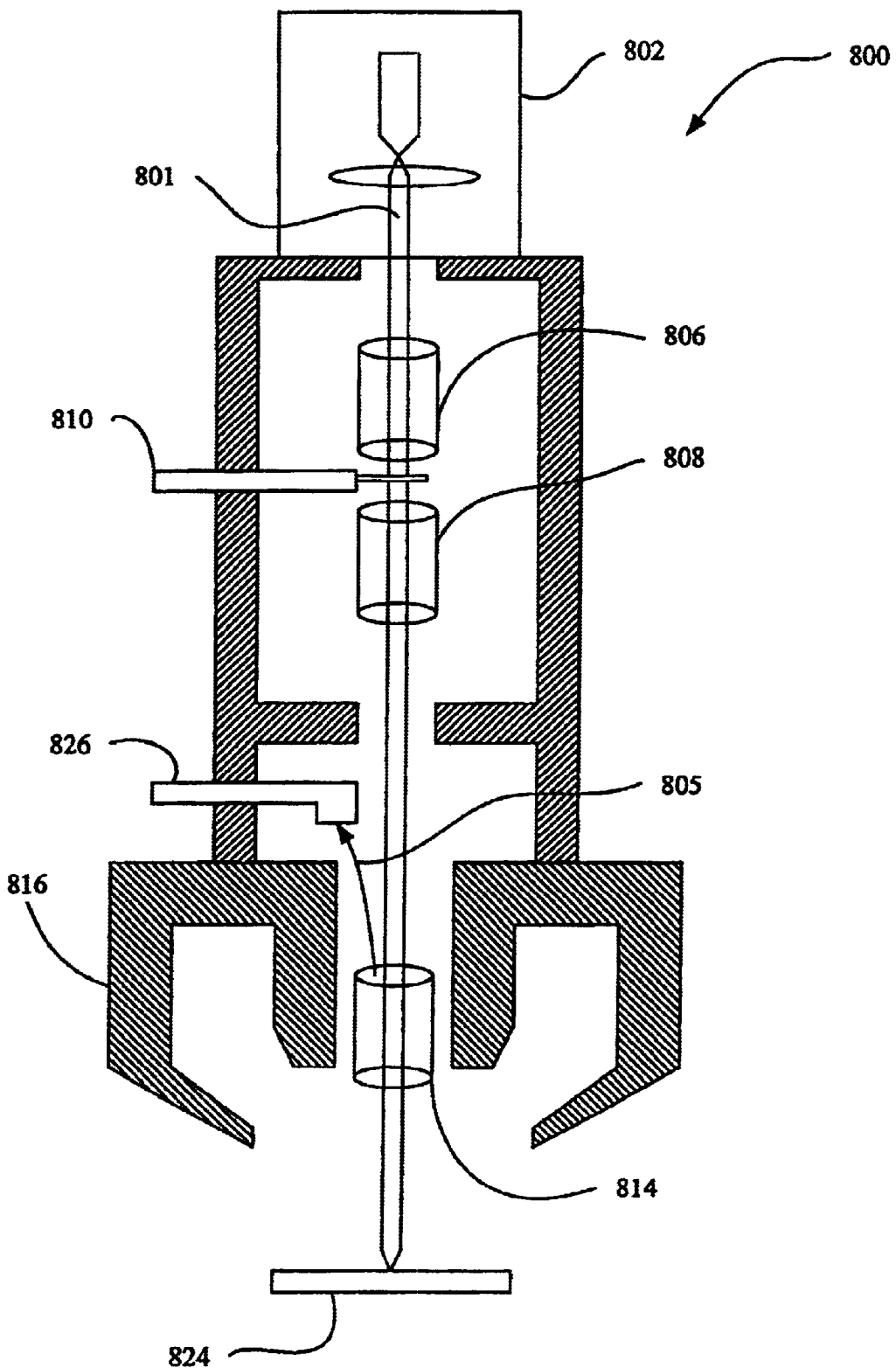
FIG. 8 is a diagrammatic representation of an electron beam that can be used to implement scanning of a sample.

A particle beam may be anything that generates current in an electrically isolated stage when a smaller amount of conductive material is provided in a scan target. In one embodiment, the particle beam can be a scanning electron microscope (SEM). FIG. 8 is a diagrammatic representation of a scanning electron microscope (SEM) 800. As shown, the SEM system 800 includes an electron beam generator (802 through 816) that generates and directs an electron beam 801 substantially toward an area of interest on a specimen 824.

In one embodiment, the electron beam generator can include an electron source unit 802, an alignment octupole 806, an electrostatic predeflector 808, a variable aperture 810, a wien filter 814, and a magnetic objective lens 816. The source unit 802 may be implemented in any suitable form for generating and emitting electrons. For example, the source unit 802 may be in the form of a filament that is heated such that electrons within the filament are excited and emitted from the filament. The octupole 806 is configured to align the beam after a particular gun lens voltage is selected.

In other words, the beam may have to be moved such that it is realigned with respect to the aperture 810.

The aperture 810 forms a hole through which the beam is directed. The lower quadrupole 808 may be included to compensate for mechanical alignment discrepancies. That is, the lower quadrupole 808 is used to adjust the alignment of the beam with respect to any misaligned through-holes of the SEM through which the beam must travel. The magnetic objective lens 816 provides a mechanism for accelerating the beam towards the sample.

Figure 9:
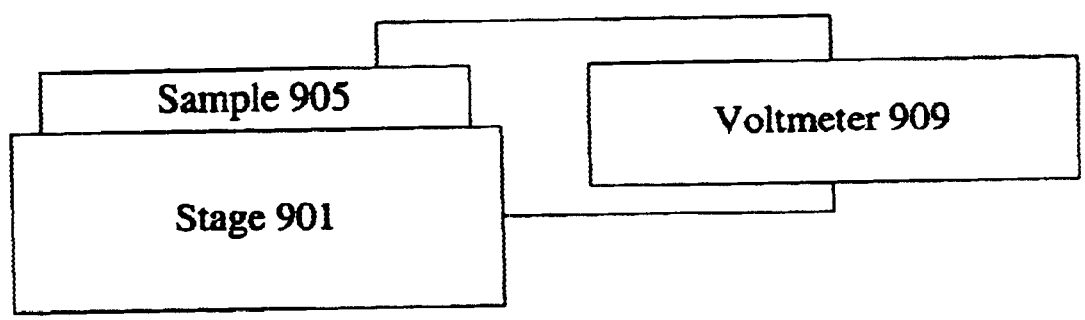
FIG. 9 is a diagrammatic representation of a stage that can be used to measure generated current.

Any suitable detector for measuring generated current may be used to implement the techniques of the present invention. FIG. 9 is a diagrammatic representation of an electrically isolated stage that can be used to implement the techniques of the present invention. A test sample 905, such as a wafer, is secured to a stage 901. According to one embodiment, the bottom surface of sample 905 is electrically connected to stage 901. Stage 901 is electrically isolated and coupled with one lead of a voltmeter 909. As will be appreciated by one of skill in the art, an ammeter or similar devices can be used instead of a voltmeter for measuring generated current. The other lead of the voltmeter 909 is electrically connected to the top surface of sample 905. In one example, when an electron beam scans a scan target of sample 905, the top surface of the sample 905 is negatively charged relative to the bottom surface, because several layers of the test sample 905 typically have resistive properties. The electrons interact with a metallization layer causing the emission of characteristic x-rays and leaving the top surface with a slight negative potential relative to the bottom surface. However, when a void exists in a particular scan target, many electrons from the electron beam do not interact with the metallization layer and pass through the sample entirely.

Although the foregoing invention has been described in some detail for purposes of clarity of understanding, it will be apparent that certain changes and modifications may be practiced within the scope of the appended claims. For example, the techniques of the present invention can be applied to defect localization, but can also be used in conjunction with thin-film measurement as described in U.S. patent application Ser. No. 09/695,726 by Shing Lee, and titled Film Thickness Measurement Using E-Beam Induced X-Ray Microanalysis as of filing on Oct. 23, 2000, the entirety of which is incorporated herein by reference for all purposes.

It should be noted that there are many alternative ways of implementing techniques of the present invention. For example, prior to performing comparisons between generated current measurements and control measurements, an entire wafer may be scanned and the corresponding measurements stored. The comparisons can then be performed after the entire wafer is scanned and the control measurement can be determined using emission measurements from the entire wafer. Accordingly, the present embodiments are to be considered as illustrative and not restrictive, and the invention is not to be limited to the details given herein, but may be modified within the scope and equivalents of the appended claims.

What is claimed is:

1. An apparatus for localizing a defect in a first scan target associated with a sample, the sample having a first surface and a second surface, the apparatus comprising:

a particle beam generator configured to scan a first scan target, the particles interacting with a first material in the scan target;

a generated current detection system configured to obtain a measurement of generated current resulting from the scan of the first scan target, wherein the measurement of generated current is compared with a control measurement to provide information for localization of a defect in the first scan target.

2. The apparatus of claim 1, further comprising an x-ray detector configured to measure x-ray emissions from the first surface.

3. The apparatus of claim 2, further comprising a stage configured to secure the sample, wherein the stage is configured to position the sample relative to the electron beam.

4. The apparatus of claim 3, wherein positioning the sample comprises rotating the sample.

5. The apparatus of claim 3, wherein the stage is electrically isolated.

6. The apparatus of claim 1, wherein the sample is a wafer comprising a plurality of integrated circuits.

7. The apparatus of claim 1, wherein the first scan target comprises a via.

8. The apparatus of claim 7, wherein the first material comprises Cu.

9. The apparatus of claim 1, wherein the control measurement is obtained by scanning an adjacent scan target.

10. The apparatus of claim 9, wherein the control measurement is obtained by scanning adjacent scan targets in the +x, −x, +y, and −y positions.

11. The apparatus of claim 10, wherein the control measurement is obtained by scanning adjacent scan targets in the +2x, −2x, +2y, and −2y positions.

12. A system for localizing a defect in a sample, the sample having a first surface and a second surface, the system comprising:

memory;

a processor coupled with memory, the processor configured to identify a first measurement of generated current resulting from a particle beam scan of a first scan target and a second measurement of x-ray emissions from the first surface, identify a control measurement, and provide the first measurement and the control measurement for comparison to thereby provide information for localizing a defect associated with the first scan target in the sample.

13. The system of claim 12, wherein the first material has low resistivity.

14. The system of claim 12, wherein the first material is copper.

15. The system of claim 12, wherein the sample is a wafer comprising a plurality of integrated circuits.

16. The system of claim 12, wherein the sample is secured to an electrically isolated stage.

17. The system of claim 12, wherein the control measurement is obtained by scanning an adjacent scan target.

18. The system of claim 12, wherein the adjacent scan target is an adjacent via.

19. The system of claim 18, wherein the control measurement is obtained by scanning adjacent scan targets in the +x, −x, +y, and −y positions.

20. The system of claim 19, wherein the control measurement is obtained by scanning adjacent scan targets in the +2x, −2x, +2y, and −2y positions.

21. The system of claim 12, further comprising identifying a first measurement of x-ray emissions characteristic of a first material associated with the first surface, the x-ray emissions resulting from the scan of the first scan target.

22. A method for localizing a defect in a sample, the method comprising:

providing a first measurement of generated current resulting from a particle beam scan of a first scan target;

providing a control measurement;

providing the first measurement and the control measurement for comparison to thereby obtain a characterization of a defect associated with the first scan target in the sample.

23. The method of claim 22, wherein the first material has low resistivity.

24. The method of claim 23, wherein the first material is copper.

25. The method of claim 22, wherein the sample is a wafer comprising a plurality of integrated circuits.

26. The method of claim 22, wherein the sample is secured to an electrically isolated stage.

27. The method of claim 22, wherein the control measurement is obtained by scanning an adjacent scan target.

28. The method of claim 22, wherein the scan target is a via.

29. The method of claim 27, wherein the adjacent scan target is an adjacent via.

30. The method of claim 29, further comprising identifying a first measurement of x-ray emissions characteristic of a first material associated with the first surface, the x-ray emissions resulting from the scan of the first scan target.

31. An apparatus for localizing a defect in a sample, the method comprising:

means for providing a first measurement of generated current resulting from a particle beam scan of a first scan target;

means for providing a control measurement;

means for providing the first measurement and the control measurement for comparison to thereby obtain a characterization of a defect associated with the first scan target in the sample.

32. The apparatus of claim 31, wherein the first material has low resistivity.

33. The apparatus of claim 32, wherein the first material is copper.

34. The apparatus of claim 31, wherein the sample is a wafer comprising a plurality of integrated circuits.

35. The apparatus of claim 31, wherein the sample is secured to an electrically isolated stage.

36. The apparatus of claim 31, wherein the control measurement is obtained by scanning an adjacent scan target.

37. The apparatus of claim 31, wherein the scan target is a via.

38. The apparatus of claim 36, wherein the adjacent scan target is an adjacent via.

39. The apparatus of claim 38, further comprising identifying a first measurement of x-ray emissions characteristic of a first material associated with the first surface, the x-ray emissions resulting from the scan of the first scan target.

* * * * *